United States Patent
Ye et al.

(10) Patent No.: US 9,424,666 B2
(45) Date of Patent: Aug. 23, 2016

(54) MEDICAL IMAGING APPARATUS AND METHOD OF RECONSTRUCTING MEDICAL IMAGE

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Jong-chul Ye, Daejeon (KR); Kyung-sang Kim, Daejeon (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 14/522,906

(22) Filed: Oct. 24, 2014

(65) Prior Publication Data

US 2015/0117742 A1    Apr. 30, 2015

Related U.S. Application Data

(60) Provisional application No. 61/895,153, filed on Oct. 24, 2013.

(30) Foreign Application Priority Data

Jan. 29, 2014    (KR) .................. 10-2014-0011731

(51) Int. Cl.
*G06K 9/00*    (2006.01)
*G06T 11/00*    (2006.01)
(Continued)

(52) U.S. Cl.
CPC ............. *G06T 11/008* (2013.01); *A61B 6/032* (2013.01); *A61B 6/503* (2013.01); *A61B 6/5205* (2013.01); *A61B 6/5288* (2013.01); *G06T 2211/412* (2013.01)

(58) Field of Classification Search
USPC .......................................................... 382/131
See application file for complete search history.

(56) References Cited

U.S. PATENT DOCUMENTS

| 8,552,402 B2 | 10/2013 | Ye et al. |
| 2012/0195458 A1 | 8/2012 | Foland et al. |

(Continued)

FOREIGN PATENT DOCUMENTS

| JP | 2005-95478 A | 4/2005 |
| JP | 2013-048713 A | 3/2013 |

(Continued)

OTHER PUBLICATIONS

Kelm, Zachary S., et al., "Optimizing Non-Local Means for Denoising Low Dose CT" IEEE International Symposium on Biomedical Imaging, IEEE, 2009, pp. 662-665.

(Continued)

*Primary Examiner* — Yon Couso
(74) *Attorney, Agent, or Firm* — Sughrue Mion, PLLC (57) ABSTRACT

A method of reconstructing a tomographic image in a medical imaging apparatus includes: acquiring a first image of an object and a second image of the object corresponding to an image to be reconstructed; determining, in the first image, a reference region corresponding to a unit region in the second image; and updating data in the unit region based on data contained in the reference region. Thus, a medical image having both high spatial resolution and high temporal resolution is reconstructed to have substantially reduced artifacts.

17 Claims, 7 Drawing Sheets

(51) Int. Cl.
*A61B 6/03* (2006.01)
*A61B 6/00* (2006.01)

(56) References Cited

U.S. PATENT DOCUMENTS

2014/0105477 A1* 4/2014 Ramirez Giraldo et al. . 382/131
2015/0112182 A1* 4/2015 Sharma et al. ................ 600/408

FOREIGN PATENT DOCUMENTS

| KR | 1998-066767 A | 10/1998 |
|---|---|---|
| WO | 2007/072279 A1 | 6/2007 |
| WO | 2013/106512 A1 | 7/2013 |

OTHER PUBLICATIONS

Wang, Guobao, et al., "Penalized Likelihood PET Image Reconstruction Using Patch-Based Edge-Preserving Regularization", IEEE Transactions on Medical Imaging, vol. 31, No. 12, pp. 2194-2204, Dec. 2012.

Dabov, Kostadin et al., "Image Denoising by Sparse 3-D Transform-Domain Collaborative Filtering" IEEE Transactions on Image Processing, vol. 16, No. 8, Aug. 2007, pp. 2080-2095.

Candes, Emmanuel J., et al., "Exact Matrix Completion via Convex Optimization", Foundations of Computational Mathematics, vol. 9, No. 6, pp. 717-772, 2009.

Chartrend, Rick, "Nonconvex Splitting for Regularized Low-Rank + Sparse Decomposition" IEEE Transactions on Signal Processing, vol. 60, No. 11, Nov. 2012, pp. 5810-5819.

Tao, Pham Dinh, et al., "A D.C. Optimization Algorithm for Solving the Trust-Region Subproblem", SIAM Journal on Optimization, vol. 8, No. 2, pp. 476-505, May 1998.

Desjardins, Benoit, et al., "ECG-Gated Cardiac CT", American Journal of Roentgenology, vol. 182, No. 4, pp. 993-1010, 2004.

Gemignani et al., "Assessment of Cardiologic Systole and Diastole Duration in Exercise Stress Tests with a Transcutaneous Accelerometer Sensor", Computers in Cardiology, pp. 153-156, 2008.

Erdogan, H. et al., "Ordered subsets algorithms for transmission tomography", Physics in Medicine and Biology, vol. 44, No. 11, pp. 2835-2851, 1999.

Kim, K. S., et al., "Globally Convergent 3D Dynamic PET Reconstruction With Patch-Based Non-Convex Lowrank Regularization", International Symposium on Biomedical Imaging, IEEE, Apr. 7-11, 2013, pp. 1158-1161.

Yuille, A. L., et al., "The Concave-Convex Procedure", Neural Computation, vol. 15, No. 4, pp. 915-936, 2003.

Segars, W. P., et al., "Realistic CT simulation using the 4D XCAT phantom", Medical Physics, vol. 35, pp. 3800-3808, Aug. 2008.

Bo Li, et al., "Image denoising with patch estimation and low patch-rank regularization", 2012 Fourth International Conference on Digital Home, IEEE, Computer Society, Nov. 2012, pp. 224-228.

Wenjia Bai, et al., "A Probabilistic Patch-Based Label Fusion Model for Multi-Atlas Segmentation With Registration Refinement: Application Cardiac MR Images", IEEE Transactions on Medical Imaging, vol. 32, No. 7, Jul. 2013, pp. 1302-1315.

Kyung Sang Kim, et al., "Low-dose Limited View 4D CT Reconstruction using Patch-based Low-rank Regularization", IEEE, 2013, 978-1-4799-0534-8, total 4 pages.

Communication from the Korean Intellectual Property Office dated Mar. 20, 2015 in a counterpart Korean application No. 10-2014-0011731.

Communication from the European Patent Office issued May 26, 2015 in a counterpart European Application No. 14189519.3.

Communication from the Korean Intellectual Property Office dated Oct. 28, 2015, in a counterpart Korean application No. 10-2014-0011731.

* cited by examiner

MEDICAL IMAGING APPARATUS AND METHOD OF RECONSTRUCTING MEDICAL IMAGE

CROSS-REFERENCE TO RELATED APPLICATIONS

This application claims priority from U.S. Provisional Application No. 61/895,153, filed on Oct. 24, 2013, and Korean Patent Application No. 10-2014-0011731, filed on Jan. 29, 2014, in the Korean Intellectual Property Office, the disclosures of which are incorporated herein in their entireties by reference.

BACKGROUND

1. Field

One or more exemplary embodiments relate to reconstructing a medical image, and more particularly, to reducing artifacts in a reconstructed medical image.

2. Description of the Related Art

Medical images obtained by computed tomography (CT) are widely used to provide medical diagnosis. High-resolution medical images are required to identify small tissue in the human body. For example, in order to discern small tissue such as coronary artery vessels, a cardiac CT requires a sub-millimeter high spatial resolution and a high temporal resolution to obtain an image of which a quality is not affected by motion of the small tissue.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include a medical imaging apparatus and a method of reconstructing a medical image which are capable of providing a medical image having both high spatial resolution and high temporal resolution and with small artifacts.

According to one or more exemplary embodiments, a method of reconstructing a tomographic image in a medical imaging apparatus includes: acquiring a reference image of an object and an image of the object to be reconstructed; determining, in the reference image, at least one reference region corresponding to a unit region in the image of the object to be reconstructed; and updating data in the unit region based on data contained in the at least one reference region.

The at least one reference region may have similar features to the unit region.

The method may further include acquiring electrocardiography (ECG) data.

The acquiring of the reference image of the object may include acquiring the reference image based on diastolic data that is data of the object obtained during a diastolic period determined based on the ECG data, and the acquiring of the image of the object to be reconstructed may include acquiring the image of the object to be reconstructed based on systolic data that is data of the object obtained during a systolic period determined based on the ECG data.

In the updating of the data in the unit region, the image of the object to be reconstructed may be reconstructed by minimizing a cost function with patch-based low rank regularization.

The updating of the data in the unit region may include: generating a matrix based on data included in the unit region and the at least one reference region; determining eigenvalues of the matrix; and updating the data in the unit region based on the determined eigenvalues.

The updating of the data in the unit region may include minimizing a cost function with respect to a matrix $w_p$; and minimizing a cost function with respect to an image x based on the result obtained by minimizing the cost function with respect to the matrix $w_p$.

The minimizing of the cost function with respect to the matrix $w_p$ and the minimizing of the cost function with respect to the image x may be iteratively performed.

In the updating of the data in the unit region, the cost function may be minimized by using a shrinkage operator.

According to one or more exemplary embodiments, a non-transitory computer-readable recording medium has recorded thereon a program for executing the above-described method on a computer.

According to one or more exemplary embodiments, a medical imaging apparatus includes an image processor that acquires a reference image of an object and an image of the object to be reconstructed, determines in the reference image at least one reference region corresponding to a unit region in the image to be reconstructed, and updates data in the unit region based on data included in the at least one reference region; and a display for displaying an image reconstructed according to the result obtained by updating the data in the unit region.

The at least one reference region may have similar features to the unit region.

The medical imaging apparatus may further include an ECG data obtainer for acquiring ECG data, wherein the image processor acquires the reference image based on diastolic data that is data of the object obtained during a diastolic period determined based on the ECG data and obtains the image of the object to be reconstructed based on systolic data that is data of the object obtained during a systolic period determined based on the ECG data.

The image processor may reconstruct the image of the object to be reconstructed by minimizing a cost function with patch-based low rank regularization.

The image processor may generate a matrix based on data included in the unit region and the at least one reference region, determine eigenvalues of the matrix, and update the data in the unit region based on the determined eigenvalues.

The image processor may minimize the cost function by using a shrinkage operator.

BRIEF DESCRIPTION OF THE DRAWINGS

The above and/or other aspects will become more apparent by describing certain exemplary embodiments, with reference to the accompanying drawings, in which.

DETAILED DESCRIPTION

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

For convenience of explanation, it is assumed herein that a medical imaging apparatus is a computed tomography (CT) apparatus.

It will be understood that when the terms "includes", "comprises", "including", and/or "comprising" when used in this specification, specify the presence of stated elements and/or components, but do not preclude the presence or addition of one or more elements and/or components thereof unless otherwise stated herein. The term "unit" as used herein means, but is not limited to, a software or hardware component, such as field-programmable gate array (FPGA) or an application-specific integrated circuit (ASIC), and performs a specific function. The 'unit' may advantageously be configured to reside on an addressable storage medium and configured to operate one or more processors. Thus, the 'unit' may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality of the components and 'units' may be combined into fewer components and 'units' or further separated into additional components and 'units'.

Expressions such as "at least one of," when preceding a list of elements, modify the entire list of elements and do not modify the individual elements of the list.

In the present specification, an "image" may refer to multi-dimensional data composed of discrete image elements (e.g., pixels in a two-dimensional (2D) image and voxels in a three-dimensional (3D) image). For example, an image may include a medical image of an object acquired by a CT apparatus.

Throughout the specification, a "CT image" may mean an image generated by synthesizing a plurality of X-ray images that are obtained by photographing an object while a CT apparatus rotates around at least one axis with respect to the object.

An "object" may include a person or an animal, or a part of a person or an animal. For example, the object may include organs such as the liver, the heart, the womb, the brain, a breast, the abdomen, or a blood vessel. Furthermore, the "object" may include a phantom. The phantom means a material having a volume that is very close to a density and effective atomic number of a living thing, and may include a sphere phantom having a property similar to a physical body.

A "user" may be, but is not limited to, a medical professional including a doctor, a nurse, a medical laboratory technologist, a medical imaging expert, and a technician who repairs a medical apparatus.

Since a CT system is capable of providing a cross-sectional image of an object, the CT system may represent an inner structure (e.g., organs such as a kidney, a lung, etc.) of the object without an overlap therebetween, compared to a general X-ray imaging apparatus.

The CT system may provide a relatively accurate cross-sectional image of an object by obtaining a plurality of pieces of image data with a thickness not more than 2 mm for several tens to several hundreds of times per second and then processing the plurality of pieces of image data. According to the related art, only a horizontal cross-sectional image of the object can be obtained, but this problem has been overcome due to various image reconstruction methods. Examples of 3D image reconstruction methods include:

- A shade surface display (SSD) method: The SSD method is an initial 3D imaging method that displays only voxels having a predetermined Hounsfield Unit (HU) value.
- A maximum intensity projection (MIP)/minimum intensity projection (MinIP) method: The MIP/MinIP method is a 3D imaging method that displays only voxels having the highest or lowest HU value from among voxels that construct an image.
- A volume rendering (VR) method: The VR method is an imaging method capable of adjusting a color and transmittance of voxels that construct an image, according to each region of interest.
- A virtual endoscopy method: This method allows an endoscopic observation in a 3D image that is reconstructed by using the VR or SSD method.
- A multi-planar reformation (MPR) method: The MPR method is used to reconstruct an image into a different cross-sectional image. An image may be reconstructed freely in a direction desired by a user.
- An editing method: This method involves editing adjacent voxels so as to allow a user to easily observe an area of interest in VR.
- A voxel of interest (VOI) method: The VOI method displays only a selected area by using VR.

Figure 1:
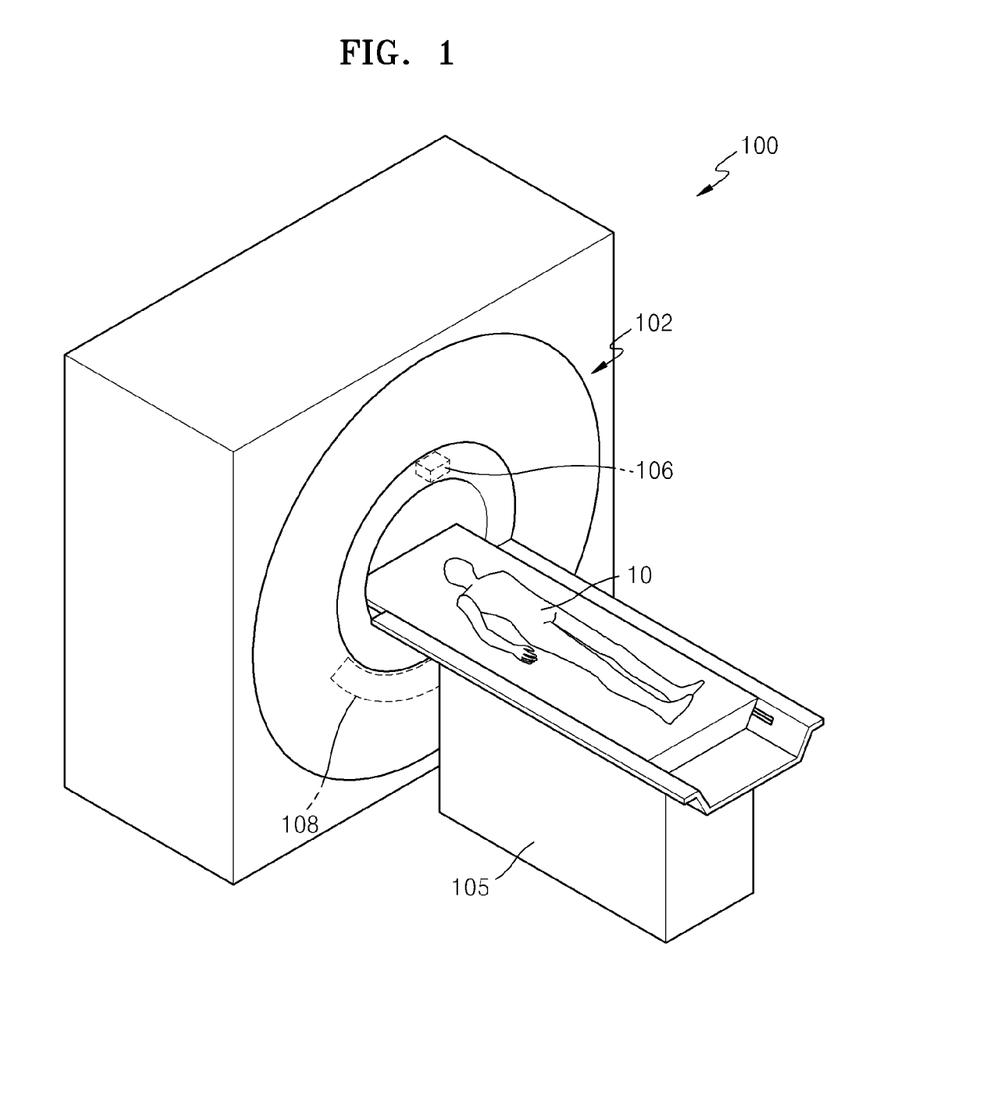
FIG. 1 is a conceptual diagram of a medical imaging apparatus according to an exemplary embodiment.

FIG. 1 is a conceptual diagram of a medical imaging apparatus 100 according to an exemplary embodiment. The medical imaging apparatus 100 according to an exemplary embodiment may be a CT system.

Referring to FIG. 1, the medical imaging apparatus 100 may include a gantry 102, a table 105, an X-ray generating unit 106, and an X-ray detector 108.

An object 10 may be positioned on the table 105.

The table 105 may move in a predetermined direction (e.g., at least one of up, down, left, and right directions) during a CT imaging procedure. The table 105 may be tilted or rotated by a predetermined degree in a predetermined direction.

The gantry 102 may also be tilted by a predetermined degree in a predetermined direction.

Figure 2:
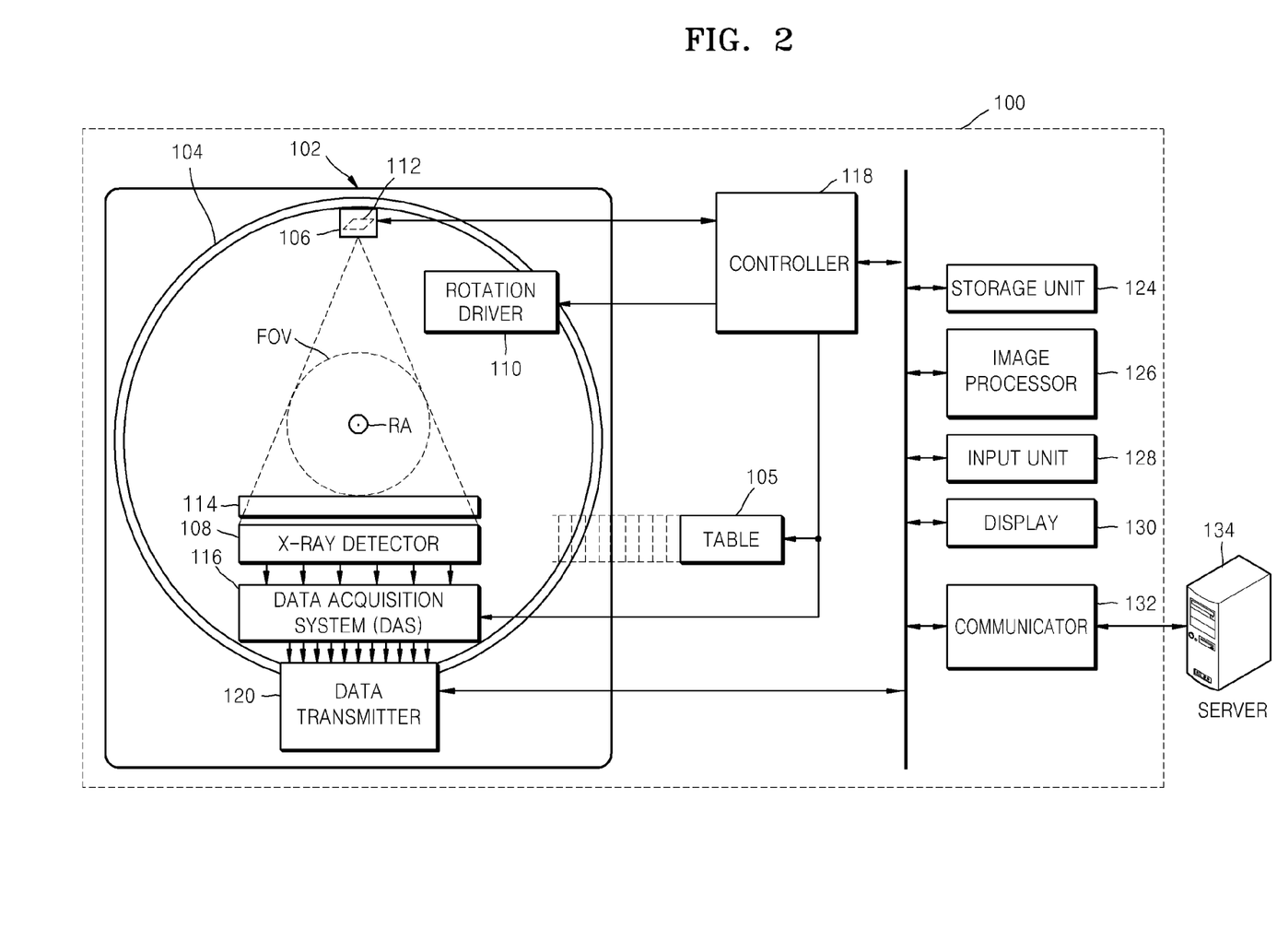
FIG. 2 is a diagram illustrating a structure of a medical imaging apparatus according to an exemplary embodiment.

FIG. 2 is a diagram illustrating a detail of the medical imaging apparatus 100.

The medical imaging apparatus 100 may include the gantry 102, the table 105, a controller 118, a storage 124, an image processor 126, an input unit 128, a display 130, and a communicator 132.

As described above, the object 10 may be positioned on the table 105. In an exemplary embodiment, the table 105 may move in a predetermined direction (e.g., at least one of up, down, left, and down directions) and movement of the table 105 may be controlled by the controller 118.

The gantry 102 may include a rotating frame 104, the X-ray generating unit 106, the X-ray detector 108, a rotation driver 110, a data acquisition system (DAS) 116, and a data transmitter 120.

The gantry 102 may include the rotating frame 104 having a loop shape capable of rotating with respect to a predetermined rotation axis (RA). Also, the rotating frame 104 may have a disc shape.

The rotating frame 104 may include the X-ray generating unit 106 and the X-ray detector 108 that face each other so as to have predetermined field of views (FOVs).

In a medical imaging system, X-ray radiation that reaches a detector (or a photosensitive film) may include attenuated primary radiation that forms a valuable image and also scattered radiation that deteriorates a quality of an image. To transmit the primary radiation and to block the scattered radiation, the rotating frame 104 may include an anti-scatter grid 114 positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driver 110 and may rotate the X-ray generating unit 106 and the X-ray detector 108 at a predetermined rotation speed. The rotating frame 104 may receive the driving signal and power from the rotation driver 110 while the rotating frame 104 contacts the rotation driver 110 via a slip ring (not shown). Furthermore, the rotating frame 104 may receive the driving signal and power from the rotation driver 110 via wireless communication.

The X-ray generating unit 106 may receive a voltage and current from a power distribution unit (PDU) (not shown) via a slip ring (not shown) and then a high voltage generating unit (not shown) and then generate and emit X-rays. When the high voltage generating unit applies a predetermined voltage (hereinafter, referred to as a tube voltage) to the X-ray generating unit 106, the X-ray generating unit 106 may generate X-rays having a plurality of energy spectrums that correspond to the tube voltage.

The X-rays generated by the X-ray generating unit 106 may be emitted in a predetermined form due to a collimator 112.

The X-ray detector 108 may be disposed so as to face the X-ray generating unit 106. The X-ray detector 108 may include a plurality of X-ray detecting elements. Each of the plurality of X-ray detecting elements may establish a single channel but is not limited thereto.

The X-ray detector 108 may detect X-rays that are generated by the X-ray generating unit 106 and transmitted via the object 10, and generate an electrical signal corresponding to intensities of the detected X-rays.

The X-ray detector 108 may include an indirect-type X-ray detector for detecting radiation after converting the radiation into light and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detector 108. The electrical signal generated by the X-ray detector 108 may be collected by the DAS 116 by wires or wirelessly. Also, the electrical signal generated by the X-ray detector 108 may be provided to an analog-to-digital converter (not shown) via an amplifier (not shown).

According to a slice thickness or the number of slices, only some of a plurality of pieces of data collected by the X-ray detector 108 may be provided to the image processor 126 via the data transmitter 120, or the image processor 126 may select only some of the plurality of pieces of data.

The digital signal may be provided to the image processor 126 via the data transmitter 120. The digital signal may be provided to the image processor 126 by wires or wirelessly.

The controller 118 may control an operation of each of the modules in the medical imaging apparatus 100. For example, the controller 118 may control operations of the table 105, the rotation driver 110, the collimator 112, the DAS 116, the storage 124, the image processor 126, the input unit 128, the display 130, the communicator 132, or the like.

The image processor 126 may receive data (e.g., pure data before a processing operation), which is obtained from the DAS 116, via the data transmitter 120, and perform pre-processing on the data.

The pre-processing may include a process of correcting sensitivity irregularity between channels, a process of correcting a signal loss due to a rapid decrease in a signal strength or due to an X-ray absorbing material such as metal or the like.

Data output from the image processor 126 may be referred as raw data or projection data. The projection data and image-capturing conditions (e.g., the tube voltage, an image-capturing angle, etc.) during acquisition of the data may be stored together in the storage 124.

The projection data may be a set of data values that correspond to the intensities of X-rays that pass through the object 10. For convenience of description, it is assumed that a set of a plurality of pieces of projection data that are simultaneously obtained from all channels at a same image-capturing degree is referred as a projection data set.

The storage 124 may include at least one storage medium from among a flash memory-type storage medium, a hard disk-type storage medium, a multimedia card micro-type storage medium, card-type memories (e.g., an SD card, an XD memory, and the like), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, a magnetic disc, and an optical disc.

The image processor 126 may also reconstruct a cross-sectional image of the object 10 by using the projection data set. The cross-sectional image may be a 3D image. In other words, the image processor 126 may reconstruct a 3D image of the object 10 by using a cone beam reconstruction method or the like, based on the projection data set.

The input unit 128 may receive an external input with respect to an X-ray tomography imaging condition, an image processing condition, or the like. For example, the X-ray tomography imaging condition may include tube voltages, setting of energy values of a plurality of X-rays, selection of an image-capturing protocol, selection of an image reconstruction method, setting of an FOV area, the number of slices, a slice thickness, setting of image post-processing parameters, or the like. Furthermore, the image processing condition may include resolution of an image, setting of attenuation coefficients of the image, setting of an image combining ratio, or the like.

The input unit 128 may include a device for receiving a predetermined input from an external source. For example, the input unit 128 may include a microphone, a keyboard, a mouse, a joystick, a touch pad, a touch pen, a voice recognition device, a gesture recognition device, or the like.

The display 130 may display an X-ray tomographic image reconstructed by the image processor 126.

Exchanges of data, power, or the like between the aforementioned elements may be performed by using at least one of wired communication, wireless communication, and optical communication.

The communicator 132 may perform communication with an external device, an external medical apparatus, etc., via a server 134. The communicator 132 may be connected to a network by wires or wirelessly and perform communication with the server 134, an external medical apparatus (not shown), or an external device (not shown). The communicator 132 may exchange data with a hospital server or other medical apparatuses in a hospital connected via a Picture Archiving and Communication System (PACS). The communicator 132 may also perform data communication with an external device (not shown) according to a Digital Imaging and Communications in Medicine (DICOM) standard.

The communicator 132 may transmit or receive data related to the examination of the object 10 via the network. Furthermore, the communicator 132 may transmit or receive a medical image obtained from other medical devices (not shown) such as a magnetic resonance imaging (MRI) apparatus, an X-ray apparatus, or the like.

Furthermore, the communicator 132 may receive a medical history or a medical treatment schedule of a patient from the server 134 and may use the medical history or the medical treatment schedule for a clinical diagnosis of the patient. The communicator 132 may perform data communication with the server 134 and/or a medical apparatus (not shown) in a hospital and with a portable terminal (not shown) of a user or patient.

The communicator 132 may also transmit information about a device error, information about a quality control status, or the like to a system manager or service personnel via the network, and receive feedback corresponding to the information.

Figure 3:
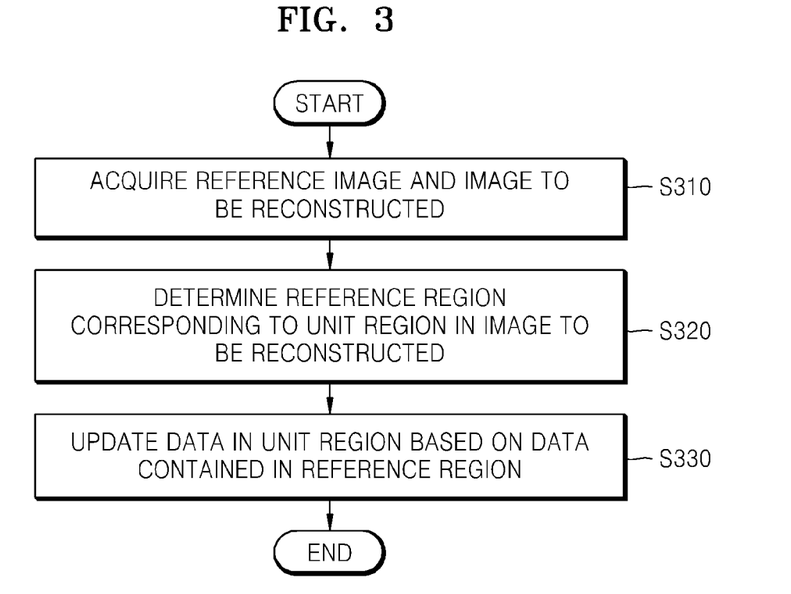
FIG. 3 is a flowchart of a process of reconstructing a medical image, according to an exemplary embodiment.

FIG. 3 is a flowchart of a process of reconstructing a medical image, according to an exemplary embodiment.

A non-negative image $x=(x_1, \ldots, x_{N_v}) \in \mathbb{R}_+^{N_v}$ may be reconstructed from noisy measured transmission data $y=(y_1, \ldots, y_{N_m}) \in \mathbb{R}_+^{N_m}$ by minimizing a cost function defined by the following Equation (1):

$$\min_x \ L(x) + \Psi_o(x) \quad (1)$$

where $L(x)$ is a negative log-likelihood term, and $\Psi o(x)$ is a patch-based low rank regularization term.

Separable Paraboloidal Surrogates

The negative log-likelihood term $L(x)$ may be minimized by using separable paraboloidal surrogates. The negative log-likelihood term $L(x)$ may be defined by Equation (2) below based on the Poisson statistics:

$$L(x) = \sum_{i=1}^{N_m} h_i([Ax]_i), \quad (2)$$

where $$h_i(k) = b_i e^{-k} + r_i - y_i \log(b_i e^{-k} + r_i)$$

Here, $b_i$ and $r_i$ denote a blank scan value and a background noise for an i-th detector element, respectively.

Since it is difficult to minimize the negative log-likelihood term $L(x)$, separable paraboloidal surrogates proposed in paper "Ordered subsets algorithms for transmission tomography," by Hakan Erdogan and Jeffrey A Fessler, *Physics in Medicine and biology*, vol. 44, no. 11, pp. 2835-2851, 1999 may be used. A quadratic surrogate function is given by Equation (3) below:

$$L(x) \leq Q_L^{(n)}(x) = \sum_i^{N_m} p_i^{(n)}([Ax^{(n)}]_i), \text{ where} \quad (3)$$

$$P_i^{(n)}(k) \triangleq h_i(k_i^{(n)}) + \dot{h}_i(k_i^{(n)})(k - k_i^{(n)}) + \frac{v_i^{(n)}}{2}(k - k_i^{(n)})^2$$

Here, n is the number of iterations,
$k_i^{(n)} = [Ax^{(n)}]_i$ and
$v_i$ is a curvature of $p_i^{(n)}(k)$.

Subsequently, a separable surrogate for a quadratic surrogate may be applied as shown in Equation (4) below:

$$[Ax]_i = \sum_j^{N_v} a_{ij} x_j = \sum_j^{N_v} g_{ij}^{(n)} \left( \frac{a_{ij}}{g_{ij}^{(n)}} (x_j - x_j^{(n)}) + [Ax^{(n)}]_i \right) \quad (4)$$

Eventually, a separable paraboloidal surrogate function $\phi_L^{(n)}(x)$ defined in Equation (5) below may be used instead of the negative log-likelihood term $L(x)$:

$$L(x) \leq Q_L^{(n)}(x) \leq \phi_L^{(n)}(x) \triangleq \sum_j^{N_v} \phi_{L,j}^{(n)}(x_j), \quad (5)$$

$$\phi_{L,j}^{(n)}(x_j) \triangleq \sum_i^{N_m} g_{ij}^{(n)} p_i^{(n)} \left( \frac{a_{ij}}{g_{ij}^{(n)}} (x_j - x_j^{(n)}) + [Ax^{(n)}]_i \right)$$

Patch-Based Low Rank Regularization

Referring to FIG. 3, a medical imaging apparatus acquires a reference image of an object and an image of the object to be reconstructed, i.e., a first image and a second image, respectively, in operation S310.

For example, a reference image is obtained based on sufficient data and may have a relatively small number of artifacts and/or the artifacts may have a relatively small size. On the other hand, an image to be reconstructed may be obtained based on insufficient data and may have a relatively great number of artifacts and/or the artifacts may have a relatively great size.

In an exemplary embodiment, the medical imaging apparatus may acquire a medical image of a periodically moving object. For example, when the medical imaging apparatus acquires a medical cardiac image, it is difficult to obtain a high-resolution medical image due to movement of the object caused by heartbeat. Thus, in order to image an object when the object moves little, the medical imaging apparatus may acquire a reference image and an image to be reconstructed by using an electrocardiography (ECG) gating technique.

Figure 4:
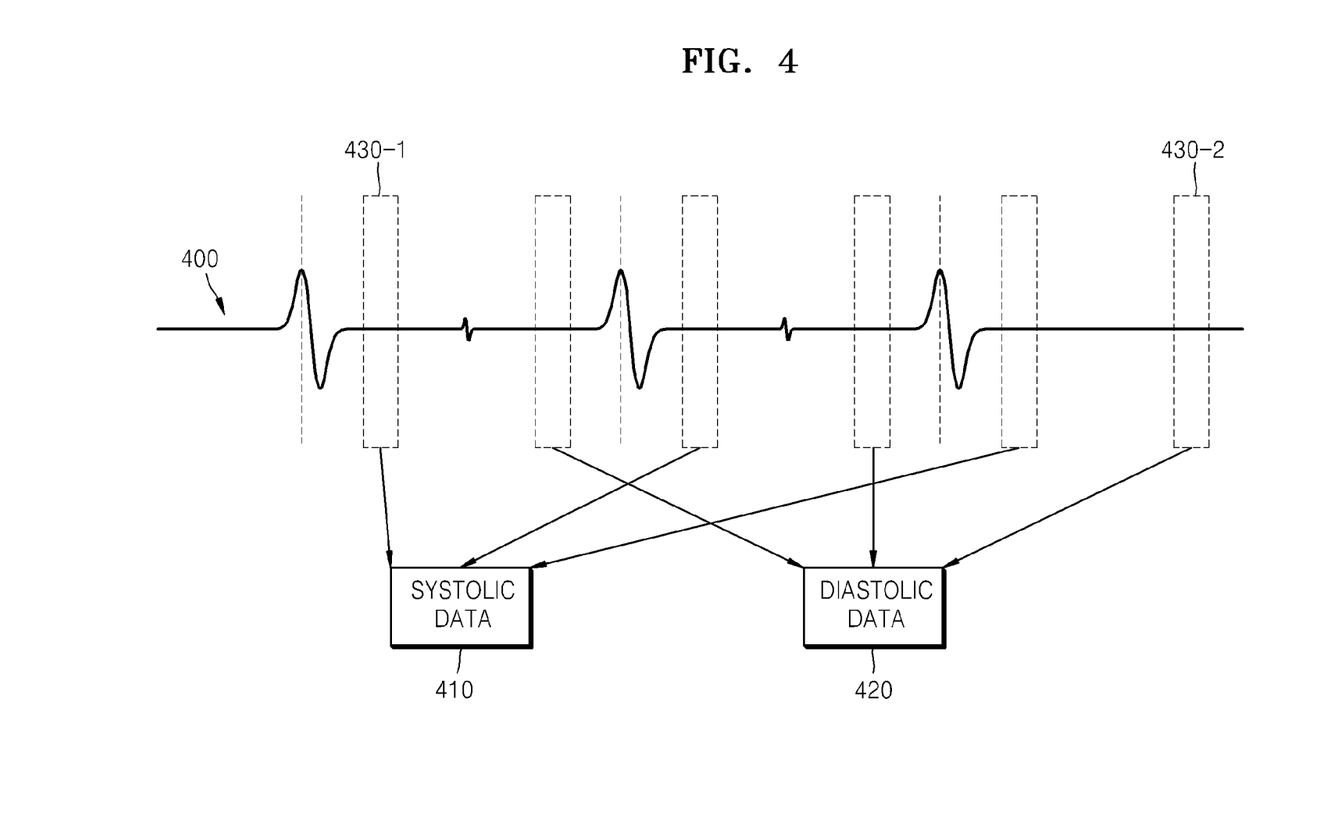
FIG. 4 is a conceptual diagram illustrating a configuration for acquiring image data based on electrocardiography (ECG) data in a medical imaging apparatus.

FIG. 4 is a conceptual diagram illustrating a configuration for acquiring image data based on ECG data 400 in a medical imaging apparatus. Referring to FIG. 4, the medical imaging apparatus may acquire the ECG data 400 by using an ECG data measuring unit therein or receive the ECG data 400 generated by an external device. The medical imaging apparatus may determine a systolic data 410 and a diastolic data 420 based on the ECG data 400. In an exemplary embodiment, the medical imaging apparatus may obtain a reference image of the object based on the diastolic data 420 that is data of the object at the diastolic period 430-2. Furthermore, the medical imaging apparatus may obtain an image of the object to be reconstructed, based on systolic data 410 that is data of the object at the systolic period 430-1. The reference image based on the diastolic data 420 may be reconstructed in advance. The reference image based on the diastolic data 420 may be used as a reference image for performing patch-based low rank regularization as described in FIG. 5 below.

Referring back to FIG. 3, after acquiring the reference image and the image to be reconstructed in operation S310, the medical imaging apparatus may determine in the reference image at least one reference region corresponding to a unit region in the image to be reconstructed (operation S320). In the present specification, the unit region may also be referred to as a patch. Each of the image to be reconstructed and the reference image may be decomposed into a plurality of unit regions called patches.

Figure 5:
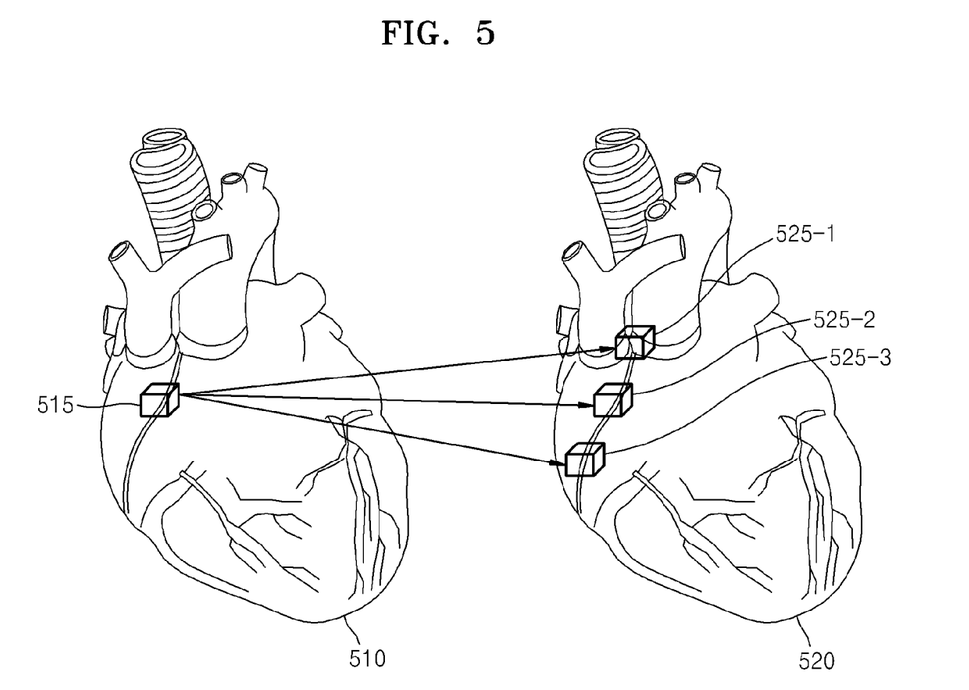
FIG. 5 is a conceptual diagram illustrating a reference region corresponding to a unit region according to an exemplary embodiment.

FIG. 5 is a conceptual diagram illustrating reference regions 525-1, 525-2, and 525-3 corresponding to a unit region 515 according to an exemplary embodiment. Referring to FIG. 5, a medical imaging apparatus may determine at least one reference region 525-1, 525-2, and 525-3 in a diastolic image 520 corresponding to the unit region 515 within an image 510 of the heart during a systolic period. According to an exemplary embodiment, the at least one reference region 525-1, 525-2, and 525-3 may have similar features to the unit region 515.

In an exemplary embodiment, patch-based low rank regularization using a group of patches may be defined in Equation (6) below:

$$\Psi_o(x, R) = \sum_{p=1}^{N_p} \lambda_p \text{Rank}(v_p), \ x = [x; \hat{x}] \text{ where}$$
$$v_p = [R_{p1}x \ R_{p2}\hat{x} \ \ldots \ R_{pQ}\hat{x}] \in \mathbb{R}^{B \times Q}$$
(6)

where $v_p$ is a matrix having data $R_{p1}x$ contained in a unit region and data $R_{pQ}\hat{x}$ contained in at least one reference region as vectors.

In other words, $R_{pq}$, q=1, ..., Q denotes a similar patch extraction operator. $\hat{x}$ may be a reference image obtained during a diastolic period.

Figure 6:
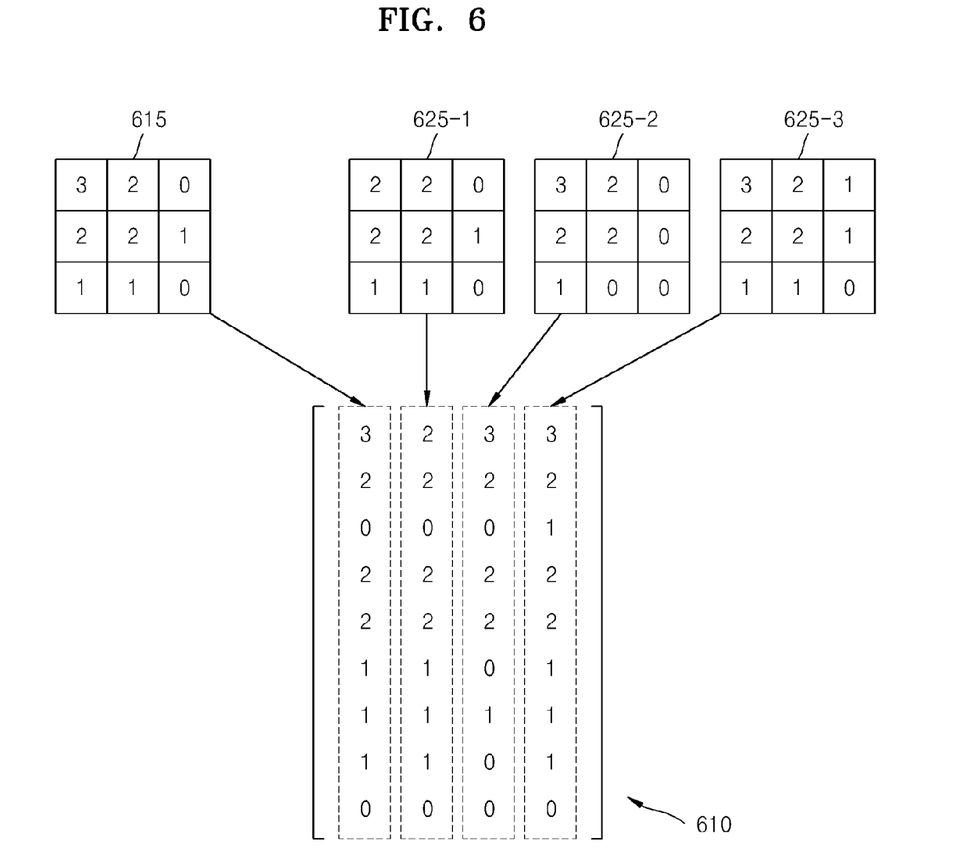
FIG. 6 illustrates an example where a medical imaging apparatus determines a matrix.

FIG. 6 illustrates an example where a medical imaging apparatus determines a matrix 610. Referring to FIG. 6, the medical imaging apparatus may determine a patch 615 from an image to be reconstructed and select at least one patch 625-1, 625-2, and 625-3 from a reference image. The medical imaging apparatus may generate the matrix 610 based on the selected patches 625-1, 625-2, and 625-3.

After performing operation S320, the medical imaging apparatus may update data in the unit region based on data contained in the at least one reference region (operation S330). To create a group of similar patches, similarity mapping relationship $\{R_{pq}\}_{p,q=1}^{P,Q_p}$ between patches needs to be determined In the similarity mapping relationship $\{R_{pq}\}_{p,q=1}^{P,Q_p}$, P is the number of pixels (voxels in a 3D image) in a patch that is a unit region, Q is the number of selected patches, and $N_p$ is the number of patch-based low rank executions.

According to exemplary embodiments, the number of patch-based low rank executions may be equal to the number of pixels (voxels in a 3D image).

To determine the similarity mapping relationship $\{R_{pq}\}_{p,q=1}^{P,Q_p}$, the medical imaging apparatus may perform refinable similarity searches. For example, the medical imaging apparatus may fix the similarity mapping relationship by using the previous estimation of an updated image x. Subsequently, the medical imaging apparatus may calculate a new estimated value from the updated image x. In detail, the medical imaging apparatus may form a matrix based on the data contained in the unit region and the at least one reference region and determine eigenvalues of the matrix. The medical imaging apparatus may update data in the unit region based on the determined eigenvalues.

Here, since a rank operator in Equation (6) is not convex, a nuclear norm may be used as a convex relaxation as shown in Equation (7) below:

$$\Psi_n(v, R) = \sum_{p=1}^{N_p} \lambda_p \|v_p\|_*.$$
(7)

where $\|v_p\|_* = \sum_{k=1}^{Rank(v_p)} \sigma_k(v_p)$ and $\sigma_k(v_p)$ is a k-th largest singular value in the matrix $v_p$.

In this case, a concave rank in Equation (8) below may be used:

$$\|v_p\|_v = \sum_{k=1}^{Rank(v_p)} h_{\mu,v}(\sigma_k(v_p)), \ 0 < v \le 1$$
(8)

According to an exemplary embodiment, a Huber function may be defined by Equation (9):

$$h_{\mu,v}(t) = \begin{cases} |t|^2/2\mu, & \text{if } |t| < \mu^{1/(2-v)} \\ |t|^v/v - \delta & \text{if } |t| \ge \mu^{1/(2-v)} \end{cases} \text{ where}$$
$$\delta = (1/v - 1/2)\mu^v/(2-v)$$
(9)

According to an exemplary embodiment, a concave-convex procedure (CCCP) may be used to solve non-convex penalty problems.

In this case, $h_{\mu,v}(t)$ is purely convex. Therefore, according to the Legendre-Fenchel transform, there exists $g_{\mu,v}$ as defined in Equation (10) below:

$$h_{\mu,v}(t) = \min_s \{|s-t|^2/\mu + g_{\mu,v}(s)\}$$
(10)

$g_{\mu,v}$ is convex when v=1, and otherwise, is generally non-convex.

Even if $g_{\mu,v}$ is not convex nor has a close form expression, a closed form solution is provided to minimize Equation (10) by using a shrinkage operator as defined by Equation (11) below:

$$\text{shrink}_v(t,\mu) = \max\{0, |t| - \mu|t|^{v-1}\} t/|t|$$
(11)

Thus, the medical imaging apparatus may perform patch-based low rank regularization as defined in Equation (12). In other words, an image to be reconstructed may be reconstructed by minimizing a cost function based on the patch-based low rank regularization.

$$\Psi(x, R) = \sum_{p=1}^{N_p} \lambda_p \|v_p\|_{h_{\mu,v}}, \quad (12)$$

$$\|v_p\|_{h_{\mu,v}} \triangleq \sum_{k=1}^{Rank(v_p)} h_{\mu,v}(\sigma_k(v_p)) = \min_{w_p}\left\{\frac{1}{\mu}\|v_p - w_p\|_F^2 + \|w_p\|_{g_{\mu,v}}\right\}$$

$$\text{where } \|w_p\|_{g_{\mu,v}} = \sum_{k=1}^{Rank(v_p)} g_{\mu,v}(\sigma_k(v_p))$$

Optimization Framework

Given R and $\hat{x}$, a minimization problem as defined in Equation (13) needs to be solved.

$$\min_x J(x) \text{ where } J(x) = \phi_L(x) + \Psi(x; \hat{x}, R) \quad (13)$$

The cost function is non-convex due to the term $\Psi(x)$. In this case, using Equations (5) and (12) may result in a minimization problem as defined in Equation (14) below:

$$\min_{x,\{w_p\}_{p=1}^{N_p}} \phi_L(x) + \sum_{p=1}^{N_p} \lambda_p\left\{\frac{1}{\mu}\|v_p - w_p\|_F^2 + \|w_p\|_{g_{\mu,v}}\right\} \quad (14)$$

The minimization problem in Equation (14) may be solved by alternatingly performing minimizations with respect to $w_p$ and x.

1. Minimization with Respect to $w_p$.

A minimization problem is independent of $\phi_L(x)$. The minimization problem may be decomposed for each patch. In detail, the following Equation (15) is given:

$$w_p^{(n+1)} = \operatorname*{argmin}_{w_p}\left\{\frac{1}{\mu}\|v_p^{(n)} - w\|_F^2 + \|w\|_{g_{\mu,v}}\right\} \quad (15)$$

A closed form solution defined in Equation (15) is given by Equation (16) below by using a shrinkage relationship in Equation (11).

$$w_p^{(n+1)} = U^{(n)} \operatorname{shrink}_v(\Sigma^{(n)}, \mu) V^{(n)H} \quad (16)$$

where $\operatorname{shrink}_v(\Sigma, \mu)$ denotes an element obtained by applying an element singular shrinkage operator.

2. Minimization with Respect to x.

Given $W^{(n+1)}$, a medical imaging apparatus may obtain a closed form solution for updating $x^{(n+1)}$. The medical imaging apparatus may also calculate a fixed point equation having a slope of a cost function with respect to $x^{(n)}$. The closed form solution is given by Equation (17):

$$x_j^{(n+1)} = \frac{d_j x_j^n - \sum_{i=1}^{N_m} a_{ij} h_i(k_i^{(n)}) + \sum_{p \in I_j} \lambda_p w_{p,j}^{(n)}}{d_j + \sum_{p \in I_j} \lambda_p}, \text{ where} \quad (17)$$

$$h_i(k_i^{(n)}) = \left(\frac{y_i}{b_i e^{-k_i^{(n)}} + r_i} - 1\right) b_i e^{-k_i^{(n)}}, \text{ and}$$

$$k_i^{(n)} = [Ax^{(n)}]_i, \; d_j = \sum_{i=1}^{N_m} a_{ij} \gamma_i (y_i - r_i)^2 / y_i, \; \gamma_i = \sum_{j=1}^{N_v} a_{ij}$$

Figure 7:
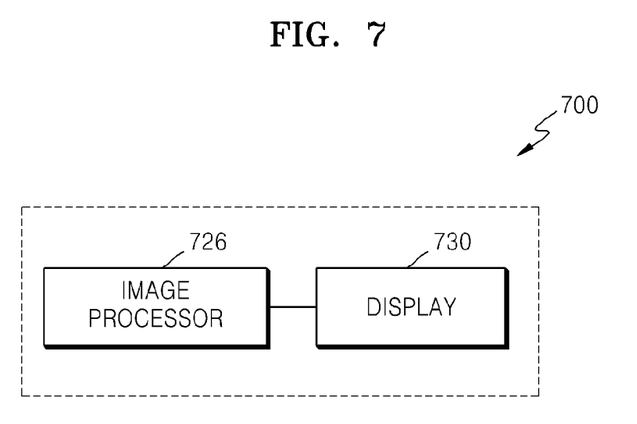
FIG. 7 is a schematic diagram of a structure of a medical imaging apparatus according to an exemplary embodiment.

FIG. 7 is a schematic diagram of a structure of a medical imaging apparatus 700 according to an exemplary embodiment.

The medical imaging apparatus 700 according to an exemplary embodiment may include an image processor 726 and a display 730. The image processor 726 may acquire a reference image of an object and an image of the object to be reconstructed. The image processor 726 may also determine in the reference image at least one reference region corresponding to a unit region in the image to be reconstructed and update data in the unit region based on data contained in the at least one reference region. The display 730 may display an image reconstructed by the image processor 726. In this case, the reference region may have similar features to the unit region.

The medical imaging apparatus 700 may further include an ECG data obtainer (not shown) for acquiring ECG data. The image processor 726 may acquire a reference image based on diastolic data that is data of the object obtained during a diastolic period as well as an image of the object to be reconstructed based on systolic data that is data of the object obtained during a systolic period.

In an exemplary embodiment, the image processor 726 may reconstruct an image to be reconstructed by minimizing a cost function using a patch-based low rank regularization algorithm. In this case, the image processor 726 may perform the patch-based low rank regularization algorithm based on Equation (12). Furthermore, the image processor 726 may use a shrinkage operator.

According to an exemplary embodiment, the image processor 726 may generate a matrix based on data contained in the unit region and the at least one reference region. The image processor 726 may also determine eigenvalues of the matrix and update data in the unit region based on the determined eigenvalues.

Exemplary embodiments may be implemented through computer-readable recording media having recorded thereon computer-executable instructions such as program modules that are executed by a computer. Computer-readable media may be any available media that can be accessed by a computer and include both volatile and nonvolatile media and both detachable and non-detachable media. Furthermore, the computer-readable media may include computer storage media and communication media. The computer storage media include both volatile and nonvolatile and both detachable and non-detachable media implemented by any method or technique for storing information such as computer-readable instructions, data structures, program modules, or other data. The communication media typically embody computer-readable instructions, data structures, program modules, other data of a modulated data signal, or other transmission mechanism, and they include any information transmission media.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

Thus, the exemplary embodiments described therein should be considered in a descriptive sense only and not for purposes of limitation. For example, each component defined as an integrated component may be implemented in a distributed fashion. Likewise, components defined as separate components may be implemented in an integrated manner.

What is claimed is:

1. A method of reconstructing a tomographic image in a medical imaging apparatus, the method comprising:
    acquiring a first image of an object and a second image of the object, the second image corresponding to the tomographic image to be reconstructed;
    determining, in the first image, a reference region corresponding to a unit region in the second image;
    updating data in the unit region in the second image based on data contained in the reference region in the first image; and
    reconstructing the second image by using the updated data,
    wherein the first image and the second image are acquired, respectively, at phases different from each other while the object is moving.

2. The method of claim 1, wherein the reference region has similar features to the unit region.

3. The method of claim 1, further comprising acquiring electrocardiography (ECG) data of the object comprising a diastolic period and a systolic period,
    wherein the acquiring the first image comprises acquiring the first image based on diastolic data of the object obtained during the diastolic period, and
    the acquiring the second image comprises acquiring the second image based on systolic data of the object obtained during the systolic period.

4. The method of claim 1, wherein the updating the data in the unit region comprises:
    updating the second image by minimizing a cost function based on a patch-based low rank regularization.

5. The method of claim 4, wherein the reconstructing the second image comprises:
    generating a matrix $v_p$ based on data included in the unit region and the reference region;
    determining eigenvalues of the generated matrix $v_p$; and
    updating the data in the unit region based on the determined eigenvalues.

6. The method of claim 5, wherein the patch-based low rank regularization is calculated as:

$$\Psi(x, R) = \sum_{p=1}^{N_p} \lambda_p \|v_p\|_{h_{\mu,\nu}},$$

$$\|v_p\|_{h_{\mu,\nu}} \triangleq \sum_{k=1}^{Rank(v_p)} h_{\mu,\nu}(\sigma_k(v_p)) = \min_{w_p}\left\{\frac{1}{\mu}\|v_p - w_p\|_F^2 + \|w_p\|_{g_{\mu,\nu}}\right\}$$

$$\text{where } \|w_p\|_{g_{\mu,\nu}} = \sum_{k=1}^{Rank(v_p)} g_{\mu,\nu}(\sigma_k(v_p)),$$

R represents a similar patch extraction operator,
Np is the number of patch-based low rank executions, which may be equal to the number of pixels,
$\Psi o(x)$ is the patch-based low rank regularization term,
$g_{\mu,\nu}$ is a value which makes equation $$h_{\mu,\nu}(t) = \min_s\{|s - t|^2/\mu + g_{\mu,\nu}(s)\}$$

and $$shrink_\nu(t,\mu)=\max\{0,|t|-\mu|t|^{\nu-1}\}t/|t| \text{ equal}$$

p is a number of pixels or voxels,
$v_p$ is the generated matrix,
$\sigma_k(v_p)$ is a k-th largest singular value in the generated matrix $v_p$,
$h_{\mu,\nu}$ is a Huber function, and
$\mu$, $\nu$ are parameters of the Huber function.

7. The method of claim 6, wherein the minimizing the cost function comprises:
    minimizing the cost function with respect to a matrix $w_p$; and
    minimizing the cost function with respect to an image x based on a result obtained by minimizing the cost function with respect to the matrix $w_p$.

8. The method of claim 7, wherein the minimizing the cost function with respect to the matrix $w_p$ and the minimizing of the cost function with respect to the image x are iteratively performed.

9. The method of claim 4, wherein, in the updating the data in the unit region, the cost function is minimized based on a shrinkage operator defined as:

$$shrink_\nu(t,\mu)=\max\{0,|t|-\mu|t|^{\nu-1}\}t/|t|.$$

10. A non-transitory computer-readable recording medium having recorded thereon a program which, when executed by a computer, causes the computer to execute the method of claim 1.

11. A medical imaging apparatus comprising:
    an image processor configured to acquire a first image of an object and a second image of the object, the second image corresponding to the tomographic image to be reconstructed, determine a reference region, in the first image, corresponding to a unit region in the second image, update data in the unit region in the second image based on data included in the reference region in the first image, and reconstruct the second image by using the updated data; and
    a display configured to display the second image which has been reconstructed according to a result obtained by updating the data in the unit region,
    wherein the first image and the second image are acquired, respectively, at phases different from each other while the object is moving.

12. The apparatus of claim 11, wherein the reference region has similar features to the unit region.

13. The apparatus of claim 11, further comprising an electrocardiography (ECG) data obtainer configured to acquire ECG data of the object comprising a diastolic period and a systolic period,
    wherein the image processor is configured to acquire the first image based on diastolic data of the object obtained during the diastolic period, and acquire the second image based on systolic data of the object obtained during the systolic period.

14. The apparatus of claim 11, wherein the image processor is configured to update the second image by minimizing a cost function based on a patch-based low rank regularization.

15. The apparatus of claim 14, wherein the image processor is configured to generate a matrix $v_p$ based on data included in the unit region and the reference region, determine eigenvalues of the generated matrix $v_p$, and update the data in the unit region based on the determined eigenvalues.

16. The apparatus of claim 15, wherein the image processor is configured to calculate the patch-based low rank regularization as:

$$\Psi(x, R) = \sum_{p=1}^{N_p} \lambda_p \|v_p\|_{h_{\mu,\nu}},$$

$$\|v_p\|_{h_{\mu,\nu}} \triangleq \sum_{k=1}^{Rank(v_p)} h_{\mu,\nu}(\sigma_k(v_p)) = \min_{w_p} \left\{ \frac{1}{\mu} \|v_p - w_p\|_F^2 + \|w_p\|_{g_{\mu,\nu}} \right\}$$

$$\text{where } \|w_p\|_{g_{\mu,\nu}} = \sum_{k=1}^{Rank(v_p)} g_{\mu,\nu}(\sigma_k(v_p)),$$

R represents a similar patch extraction operator,
Np is the number of patch-based low rank executions, which may be equal to the number Of pixels,
$\Psi_0(x)$ is the patch-based low rank regularization term,
$g_{\mu,\nu}$ is a value which makes equation $$h_{\mu,\nu}(t) = \min_s \{|s - t|^2 / \mu + g_{\mu,\nu}(s)\}$$

and $$\text{shrink}_\nu(t,\mu) = \max\{0, |t| - \mu|t|^{\nu-1}\} t/|t| \text{ equal},$$

p is a number of pixels or voxels,
$v_p$ is the generated matrix,
$\sigma_k(v_p)$ is a k-th largest singular value of the generated matrix $v_p$,
$h_{\mu,\nu}$ is a Huber function, and
$\mu$, $\nu$ are parameters of the Huber function.

17. The apparatus of claim 11, wherein the image processor is configured to minimize the cost function based on a shrinkage operator defined as:

$$\text{shrink}_\nu(t,\mu) = \max\{0, |t| - \mu|t|^{\nu-1}\} t/|t|.$$

* * * * *